United States Patent [19]

Stief

[11] Patent Number: 5,492,911

[45] Date of Patent: Feb. 20, 1996

[54] LINSIDOMINE FOR THE TREATMENT FOR ERECTILE DYSFUNCTIONS

[75] Inventor: Christian Stief, Rehmenbreiten 6, W-3005 Hemmingen-Westerfeld, Germany

[73] Assignee: Christian Stief, Hemmingen, Germany

[21] Appl. No.: 146,204

[22] PCT Filed: May 14, 1992

[86] PCT No.: PCT/EP92/01109

§ 371 Date: Nov. 17, 1993

§ 102(e) Date: Nov. 17, 1993

[87] PCT Pub. No.: WO92/21346

PCT Pub. Date: Dec. 10, 1992

[30] Foreign Application Priority Data

May 27, 1991 [DE] Germany .......................... 41 17 249.3

[51] Int. Cl.⁶ ................................................ A61K 31/535
[52] U.S. Cl. ........................... 514/252; 544/367; 514/906; 514/968
[58] Field of Search ................................... 514/906, 968, 514/252; 544/367

[56] References Cited

U.S. PATENT DOCUMENTS

| | | | |
|---|---|---|---|
| 3,312,690 | 4/1967 | Masuda et al. | 514/252 |
| 4,421,754 | 12/1983 | Hidaka et al. | 544/367 |
| 4,687,771 | 8/1987 | Gamble et al. | 514/253 |
| 4,801,587 | 1/1989 | Voss et al. | 514/248 |
| 4,840,952 | 6/1989 | Gamble et al. | 514/253 |
| 4,931,445 | 6/1990 | Goldstein et al. | 514/252 |
| 5,059,603 | 10/1991 | Rubin | 514/264 |
| 5,110,820 | 5/1992 | Fujikura et al. | 514/356 |
| 5,145,852 | 9/1992 | Virag | 514/253 |
| 5,155,109 | 10/1992 | Schönafinger et al. | 514/252 |
| 5,214,030 | 5/1993 | Stief | 514/12 |
| 5,236,904 | 8/1993 | Gerstenberg et al. | 514/12 |
| 5,256,652 | 10/1993 | El-Rashidy | 514/307 |
| 5,267,963 | 12/1993 | Bachynsky | 604/134 |
| 5,298,496 | 3/1994 | Vikmon et al. | 514/58 |

OTHER PUBLICATIONS

The FASEB Journal, vol. 5, No. 4, Mar. 1991, 2 pages, No. 175.
The Physiological Society, The Journal of Physiology, vol. 438, 1991, p. 103 p.
Acta Physiologica Scandinavica, vol. 141, No. 3, Mar. 1991, 3 pages, pp. 441–442.
Characterization of Inhibitory Neurotransmission in the Isolated Corpus Cavernosum from Rabbit and Man. F. Homquist, et al. pp. 109–130 Lund University doctoral dissertation 20 Sep. 1991.
The Journal of Urology, vol. 9, No. 4, 1991, 4 pages, pp. 237–239.
Schwellkorper–Autoinjektionstherapie (SKAT): erste Erfahrungen bei erektiler Dysfunktion, C. G. Stief et al., 5 pages, pp. 63–66.
Blood Vessels, Form and Functio nof Blood and Lymphatic Vessels, Mechanisms of Vasodilatation, Jul. 5–7, 1989, 14 pages, pp. 282–294.
The Journal of Urology, Aua Eighty–Seventh Annual Meeting, May 10–14, 1992, 2 pages, No. 205.
International Search Report, Aug. 10, 1992.

*Primary Examiner*—Ronald W. Griffin
*Attorney, Agent, or Firm*—Perman & Green

[57] ABSTRACT

The treatment of erectile dysfunctions in mammals, including humans, comprises administering to a host in need thereof an effective dose of linsidomine or a pharmacologically compatible salt thereof, alone or in combination with adenosine, vitamins, prostaglandins, calcium antagonists, α-receptor blockers and/or smooth muscle relaxants. Also disclosed is a disposable medicament pack containing in a sterile package a disposable syringe containing a dose unit of an erection-promoting active substance or of a combination of active substances, sterile swabs provided with disinfectants, and instructions for use.

11 Claims, 4 Drawing Sheets

(before SIN-1)

(4' after SIN-1)

FIG. 3 (7' after SIN-1)

(85' after SIN-1)

LINSIDOMINE FOR THE TREATMENT FOR ERECTILE DYSFUNCTIONS

The invention relates to the use of linsidomine and its pharmacologically compatible salts for the treatment of erectils dysfunctions.

About 5% of men in the 40th year of life and 20% in the 60th year of life suffer from an erectils dysfunction. The loss of potency is a shock to the man's, in particular the young man's, view of himself in physical, emotional and social terms. Patients with chronic erectils dysfunction are unsure of their sexuality and personality and should be regarded as ill.

Disturbances of potency, which were mainly attributed to psychological causes until the 1970s, have been treated, besides psychotherapeutic measures, by use of testosterones or of aphrodisiacs of disputed value. Not until the physiology of the process of erection was investigated was it found that in more than 60% of patients the erection impairments are brought about by organic causes, with contributions from autonomic efferences from the parssympathetic portion of the sacral region of the spinal cord, neurotransmitters, dilatation of the penis arteries, relaxation of the cavernous spaces and constriction of the veins. In more than 70% of cases there is causal involvement of vascular factors such as pathological arterial blood supplies or abnormally increased venous outflow from the cavernous spaces. Neurogenic disturbances are involved to the extent of about 20%.

Oral therapy of these organic dysfunctions with vasoactive substances such as yohimbine, phenoxybenzamine, terbutaline, bethanechol, levodopa, verapamil or theophylline has proved unsuccessful. Besides the use of prosthetic implants or revascularization operations, success has been achieved with intracavernous injection of papaverine (Virag, Lancet, 2, 938, 1982), the α-receptor blocker phenoxybenzamine (Brindley, Br. J. Psychiatr., 143, 332, 1983) and a combination of papaverine and the d-receptor blocker phentolemine (Stief, Urologe A, 25, 63, 1986). The latter therapeutic method can be carried out by the patient himself and is also called cavernous body autoinjection therapy (CBAT).

However, the disadvantages which have emerged are in some cases undesired prolonged erection with the risk of priapism on use of papaverine, undesired painfulness on use of phenoxybenzamine and a possible carcinogenicity of this compound.

In addition, in an animal experiment (Cynomolgus) with 1–2 intracavernous injections of papaverine each week for 12 months there was found to be extensive fibrosis of wide parts of the cavernous body, which would lead to extremely adverse long-term results in humans because erection is no longer possible when there is fibrosis of the corpus cavernosum.

The use of acetylcholine is, while the erection is only short-lasting, associated with severe systemic side effects, and the injection of prostaglandin $E_1$ is refused by patients because the pain is too great.

The object of the invention was therefore to develop and produce medicaments for the treatment of neurogenic, arterial, neurotransmitter-related, myopathic, venous and psychogenic erectile dysfunctions in mammals, preferably in humans, without the said side effects. It has now been found, surprisingly, that intracavernous injection of linsidomine hydrochloride leads to erection with complete rigidity.

The invention therefore relates to the use of 3-morpholinosydnone imine (linsidomine, SIN-1) and its pharmacologically compatible salts, preferably linsidomine hydrochloride, for the production of medicaments for the treatment of erectile dysfunctions in mammals, preferably in humans, and to the treatment of erectile dysfunctions in mammals and humans.

The invention also relates to the use of linsidomine which has been converted, for pharmaceutical reasons, into the pharmacologically compatible salts. The salts are obtained in a conventional way, by neutralizing the base with inorganic or organic acids.

Suitable inorganic acids are, for example, hydrochloric acid, sulfuric acid, phosphoric acid or hydrobromic acid, and of organic acids are, for example, carboxylic, sulfo or sulfonic acids such as acetic acid, tartaric acid, lactic acid, propionic acid, glycolic acid, malonic acid, maleic acid, fumaric acid, tannic acid, succinic acid, alginic acid, benzoic acid, 2-phenoxybenzoic acid, 2-acetoxybenzoic acid, cinnamic acid, mandelic acid, citric acid, malic acid, salicylic acid, 3-aminosalicylic acid, ascorbic acid, embonic acid, nicotinic acid, isonicotinic acid, oxalic acid, amino acids, methanesulfonic acid, ethanesulfonic acid, 2-hydroxyethanesulfonic acid, ethane-1,2-disulfonic acid, benzenesulfonic acid, 4-methylbenzenesulfonic acid or naphthalene-2-sulfonic acid. The medicaments used according to the invention contain, besides the conventional ancillary substances, vehicles and additives, an effective dose of linsidomine or of one of its salts for the treatment of the said dysfunctions. The dosage depends on the species, body weight, age, individual condition and mode of administration.

Suitable administration forms are both parenteral and topical formulations such as, for example, lotions, creams, solutions, gels, sprays, elastic liquid plasters, transdermal systems or coatings for condoms.

Parenteral administration is preferred because it is the most reliable form for targeted insertion of a targeted amount of active substance directly without broad falsification by other factors.

Particularly preferred for simplified use is also a sterile administration kit for single use, which, besides sterile swabs provided with disinfectant solutions and the relevant information for use, contains disposable syringes for simplified use with a dose unit of an effective amount of an erection-promoting agent, preferably of a parenteral presentation of linsidomine. The said disposable prefilled syringes are preferably of the ultrafine type as used, for example, in insulin therapy. Also preferred are syringes of the autoinjector type which are even simpler to manipulate. The prefilled syringes are constructed in preferred form in opaque [lacuna] because this makes the addition of photostabilizers to the parenteral formulations unnecessary. However, they can also be designed so that active substance and relevant injection solvent are mixed only immediately before the injection. This can take place, for example, in two-container ampoules or syringes. It is then likewise possible in this way for an addition of a photostabilizer which is necessary where appropriate to be dispensed with.

The sterile swabs for the disinfection contain the conventional agents for skin disinfection such as, for example, ethanol. However, they can moreover also additionally contain erection-promoting agents in a form which can be administered topically to increase or prolong the effect. Formulations for parenteral administration contain 0.1 to 5 mg, preferably 0.1 to 2 mg, of linsidomine per dose unit and can be in the form of separate dose unit forms such as, for example, ampoules or vials. Solutions of the active substance are preferably used, preferably aqueous solutions, but also suspensions. These injection forms can be made available as ready-to-use product or be prepared only immediately before use by mixing the active compound, for example, the lyophilisate, where appropriate with other solid vehicles, with the desired solvent or suspending agent. It is self-evident that a higher concentration of active substance is indicated for topical administration forms than mentioned for parenteral formulations.

Both parenteral and topical forms can be sterilized and/or contain, where appropriate, ancillary substances such as preservatives, stabilizers, wetting agents, penetration promoters, emulsifiers, spreading agents, solubilizers, salts to control the osmotic pressure or for buffering and/or viscosity regulators.

Examples of additives of these types are tartrate and citrate buffers, ethanol, complex images [sic] (such as ethylenediaminetetraacetic acid and its non-toxic salts). Suitable for controlling the viscosity are high molecular weight polymers such as, for example, liquid polyethylene oxide, carboxymethylcelluloses, polyvinylpryrrodilones [sic], dextrans or gelatin. Examples of solid vehicles are starch, lactose, mannitol, methylcellulose, talc, highly disperse silicas, high molecular weight fatty acids (such as stearic acid), gelatin, agar-agar, calcium phosphate, magnesium stearate, animal and vegetable fats, solid high molecular weight polymers (such as polyethylene glycol.

Oily suspensions for parenteral or topical uses can be vegetable synthetic oils such as, for example, liquid fatty acid esters with in each case 8 to 22 C atoms in the fatty acid chains, for example palmitic, lauric, tridecylic, margaric, stearic, arachic, myristic, behen-pentadecylic, linoleic, elaidic, brasidin, erucic or oleic acid, which be esterified [sic] with mono- to trihydric alcohols with 1 to 6 C atoms such as, for example, methanol, ethanol, propanol, butanol, pentanol or their isomers, glycerol or glycerol. Examples of fatty acid esters of these types are commercially available Miglyols, isopropyl myristate, isopropyl palmirate, isopropyl stearate, PEG 6-capric acid, caprylic/capric esters of saturated fatty alcohols, polyoxyethylene glycerol trioleates, ethyl oleate, waxlike fatty acid esters such as artificial duck preen gland fat, coconut fatty acid isopropyl ester, oleyl oleate, redecyl [sic] oleate, ethyl lactate, dibuthyl [sic] phthalate, diisopropyl adipate, polyol fatty acid esters and others. Likewise suitable are silicone oils of various viscosity or fatty alcohols such as isotridexyl [sic] alcohol, 2-octyldodecanol, cetylstearyl alcohol or oleyl alcohol, fatty acids such as, for example, oleic acid. It is also possible to use vegetable oils such as castor oil, almond oil, olive oil, sesame oil, cottonseed oil, peanut oil or soybean oil. The said substances additionally have the properties of a spreading agent, that is to say particularly good distribution on the skin takes place.

Suitable solvents, gel formers and solubilizers are water or solvents which are miscible with water. Suitable examples are alcohols such as, for example, ethanol or isopropyl alcohol, benzyl alcohol, 2-octyldodecanol, polyethylene glycols, phthalates, adipates, propylene glycol, glycerol, di- or tripropylene glycol, waxes, Methylcellosolve, Cellosolve, esters, morpholines, dioxane, dimethyl sulfoxide, dimethylformamide, tetrahydrofuran, cyclohexanone etc.

Film formers which can be used are cellulose ethers which can dissolve or swell both in water and in organic solvents and, after drying, form a type of film, such as, for example, hydroxypropylcellulose, methylcellulose, ethylcellulose or soluble starches.

Mixed forms between gel formers and film formers are likewise entirely possible. Used for this purpose are, in particular, ionic macromolecules such as, for example, sodium carboxymethylcellulose, polyacrylic acid, polymethacrylic acid and their salts, sodium amylopectin semiglycolate, alginic acid or propylene glycol alginate as sodium salt, gum arabic, xanthan gum, guar gum or carrageenan.

Other formulation auxiliaries which can be employed are: glycerol, paraffin of various viscosity, triethanolamine, collagen, allantoin, novantisolic acid, perfume oils.

It may also be necessary to use surfactants, emulsifiers or wetting agents for the formulation, such as, for example, Na lauryl sulfate, fatty alcohol ether sulfates, di-Na N-lauryl-β-iminodipropionate, polyethoxylated castor oil or sorbitan mono-oleate, monostearate, cetyl alcohol, lecithin, glycerol monostearate, polyoxyethylene stearate, alkylphenol polyglycol ethers, cetyltrimethylammonium chloride or mono-/dialkyl polyglycol ether orthophosphoric acid monoethanolamine salts.

Stabilizers such as montmorillonites or colloidal silicas for stabilizing emulsions or for preventing the breakdown of the active substances such as antioxidants, for example tocopherols or butylated hydroxyanisole, or preservatives such as p-hydroxybenzoic esters, may likewise be necessary where appropriate for preparing the desired formulations.

To promote penetration, transdermal formulations preferably contain organic solvents which are well tolerated by the skin, such as ethanol, methylpyrrolidone, polyethylene glycol, oleyl alcohol, octanol, linoleic acid, triacetin, propylene glycol, glycerol, Solketal or dimethyl sulfoxide.

As a consequence of the sensitivity of linsidomine to light it is indicated to add photostabilizers to the dosage forms, or to provide them in appropriately light-protected packages such as, for example, in opaque disposable prefilled syringes.

Suitable photostabilizers are compounds such as quinolines, for example 8-hydroxyquinoline or quinoline yellow; suitable foodstuff colorants; flavanoids such as, for example, hesperidin, hesperidin methylchalcone, hesperidin phosphate, hesperitin [sic], quercetin, quercitrin, rutin, rutin sulfate, naringenin, kaempferol 7,4'-dimethyl ether, morin, apigetrin, luteolin and its 7-glycoside or troxerutin. They are added to the linsidomine in the ratio of amounts from 0.001:1 to 50:1, preferably 0.1:1 to 20:1.

The production, packaging and sealing of the products takes place under the conventional antimicrobial and aseptic conditions. Packaging for topical or transdermal use also takes place where possible in separate dose units to facilitate manipulation, in this case too, as for parenteral forms, where appropriate for stability reasons by separate packaging of the active substances or their combinations as lyophilisate, where appropriate with solid vehicles, and the required solvents etc.

Another aspect of the invention is the use of linsidomine in combination with synergistically acting substances such as adenosine, vitamins, for example vitamin A or H, prostaglandins, for example $E_1$ with peptides such as, for example, calcitonine gens related peptides (CGRP), with calcium antagonists such as nifedipine, verapamil, diltiazem, gallopamil, niludipine, nimodipins, nicardipine, prenylamine, fendiline, terodiline, nisaldipine, nitrendipine or perhexiline. Other possible combinations are with α-receptor blockers, for example phentolamine methanesulphonate, phenoxybenzamine or minoxidil, or smooth muscle relaxants such as papaverine, trinitroglycerine, sodium nitroprusside or S-nitroso-N-acetylpenicillamine.

The following examples of possible pharmaceutical formulations are intended exclusively to illustrate the teaching according to the invention but by no means to limit it.

Example 1

Injection solution 400 mg of linsidomine hydrochloride are dissolved with 750 mg of NaCl in distilled water, adjusted to pH 3.7 with 1N HCl and made up to 100 ml with distilled water and packaged in 0.5 ml ampoules.

Example 2

Solution for topical administration

A solution for topical administration was prepared from 3.2 g of linsidomine hydrochloride, 2 ml of isopropyl myristate and 10 ml of ethanol and packaged to give dose units of 2 ml each.

Example 3

Transdermal plaster 10 g of linoleic acid and 90 g of propylene glycol are mixed. 40 g of linsidomine hydrochloride are dissolved in this mixture. Squares of gauze coated on one side with plastic are impregnated with the solution and sealed in aluminum foil.

Example 4

Spreadable gel 94 g of purified water are heated to 70° C., and 80 g of linsidomine hydrochloride are added. Addition of 0.2 g of p-hydroxybenzoic ester is followed by dispersion of 5 g of methylhydroxyethylcellulose in the resulting solution. It is then cooled while stirring. After cooling, a high-viscosity gel with a viscosity of 90 Pa.s is obtained.

Example 5

Oil-in-water emulsion

In a first mixture, 7 g of a mixture composed of saturated fatty acids, fatty alcohols, wool wax, mineral oils and non-ionic emulsifiers is melted homogeneously together with 2.5 g of polyethylene glycol glycerol fatty acid ester, 3 g of monoglycerides of stearic and palmitic acids, 0.3 g of cetyl alcohol and 3.0 g of isopropyl palmirate by heating to 70° C. in a water bath. In a second mixture, 80 g of purified water are mixed with 3 g of propylene glycol while stirring and heated to 70° C. The mixture obtained in this way is then mixed with 40 g of linsidomine hydrochloride and 200 mg of a preservative. The resulting clear solution is emulsified in the first mixture by stirring at 70° C. The emulsion obtained in this way is cooled to 40° C., and the loss of water suffered owing to evaporation is replenished. The emulsion is cooled to 30° C. and then packaged.

Example 6

Liquid plaster 40 g of linsidomine hydrochloride are dissolved in a mixture of 5 g of benzyl alcohol, 6 g of isopropyl stearate or an identical amount of an isopropyl myristate/isopropyl palmirate/isopropyl stearate mixture, 10 g of vinylpyrrolidone/vinyl acetate copolymer and 89 g of isopropanol. The solution can be packaged in separate dose units for liquid administration or as spray with conventional propellants.

Example 7

Oil-water emulsion

A mixture of 40 g of linsidomine hydrochloride, 9 g of a mixture of mono- and diglycerides of palmitic and stearic acids, 3 g of cetylstearyl alcohol with about 12 mol of ethylene oxide, 10 g of 2-octyldodecanol, 5 g of high viscosity paraffin, 5 g of benzyl alcohol, 500 mg of PHB esters and demineralized water ad 100 g is prepared by conventional methods.

Example 8

Soft-consistency cream

A cream of this type contains, for example, 40 g of linsidomine hydrochloride, 4 g of mono- and diglycerides of palmitin and stearic acid, 4 g of cetyl palmirate, 1 g of cetylstearyl alcohol with about 12 mol of ethylene oxide, 1 g of cetylstearyl alcohol with about 30 mol of ethylene oxide, 5 g of isopropyl myristate/isopropyl palmitate/isopropyl stearate mixture, 0.5 g of slightly crosslinked polyacrylic acid of extremely high MW, 0.11 g of 45% strength sodium hydroxide, 3 g of glycerol and demineralized water ad 100 g.

Example 9

Non-greasy emulsion

A mixture of 2.5 g of decyl oleate, 2.5 g of isopropyl myristate, 4 g of low viscosity paraffin, 0.9 g of polyethylene stearate, 0.6 g of sorbitan and glycerol fatty acid esters are stirred and melted at 70° C. for 10 min. The molten mixture is added to a solution, at 75° C., of 50 g of demineralized water, 4 g of linsidomine hydrochloride and 100 mg of allantoin while stirring and is cooled to 45° C. At this temperature, a Carbopol mucilage composed of 10 g of ethanol, 0.7 g of Carbopol 934 (slightly crosslinked polyacrylic acid) and 22.95 g of demineralized water is added, which has been dispersed with Turrax, subsequently swollen for 2 h and neutralized with 0.15 g of 45% strength sodium hydroxide solution. When 40° C. is reached, 1 g of collagen is then also added. Finally, the crude emulsion is homogenized, where appropriate after an addition of 0.6 g of perfume oil, at 20° to 25° C. in a high pressure homogenizer.

Example 10

Gelatin solution

For a gelatin solution, 2 mg of linsidomine hydrochloride, 150 mg of gelatin, 4.7 mg of phenol are made up to 1 ml with distilled water and packaged in 1 ml vials.

Example 11

Spray 1 g of linsidomine hydrochloride is suspended in a mixture of 3.5 ml of Miglyol 812 and 0.08 g of benzyl alcohol. This suspension is introduced into a container with metering valve. 5 ml of Freon 12 are now introduced into the container through the valve under pressure. The Freon is dissolved in the Miglyol/benzyl alcohol mixture by shaking.

The activity of the medicaments for the teaching according to the invention is demonstrated by the following study:

A dose-dependent erection without systemic side effects was achieved in eight men by intracavernous injection of 0.01 to 2 mg of linsidomine hydrochloride. The dramatic increase in the arterial inflow into the cavernous body after intracavernous injection of 0.2 mg of linsidomine hydrochloride in a patient with erectile dysfunction is depicted in FIGS. 1 to 4. The Doppler sonographies show the flow rate of the blood in a penis artery.

Figure 1:
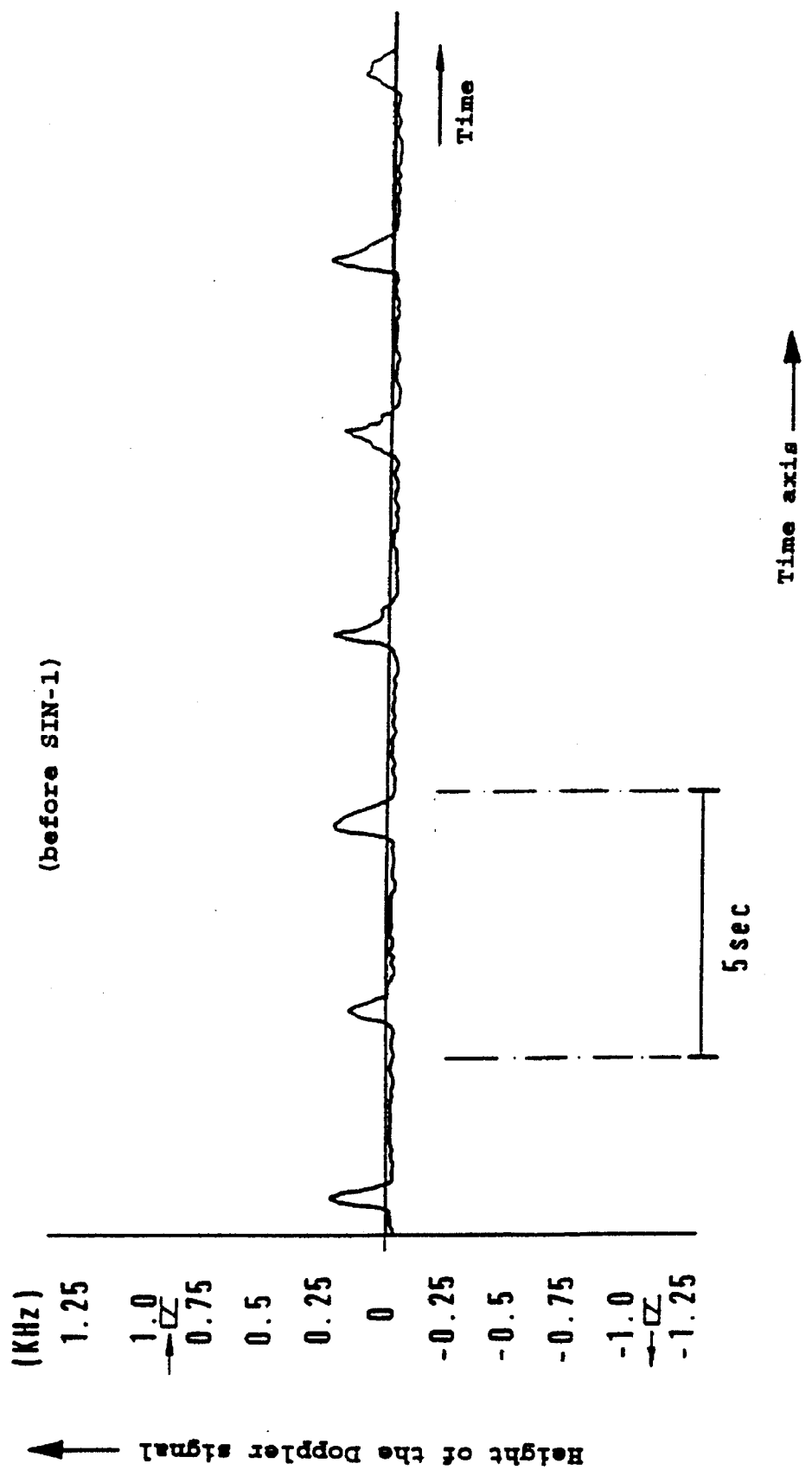
FIG. 1 shows the normal flow rate before administration of linsidomine hydrochloride.
Figure 2:
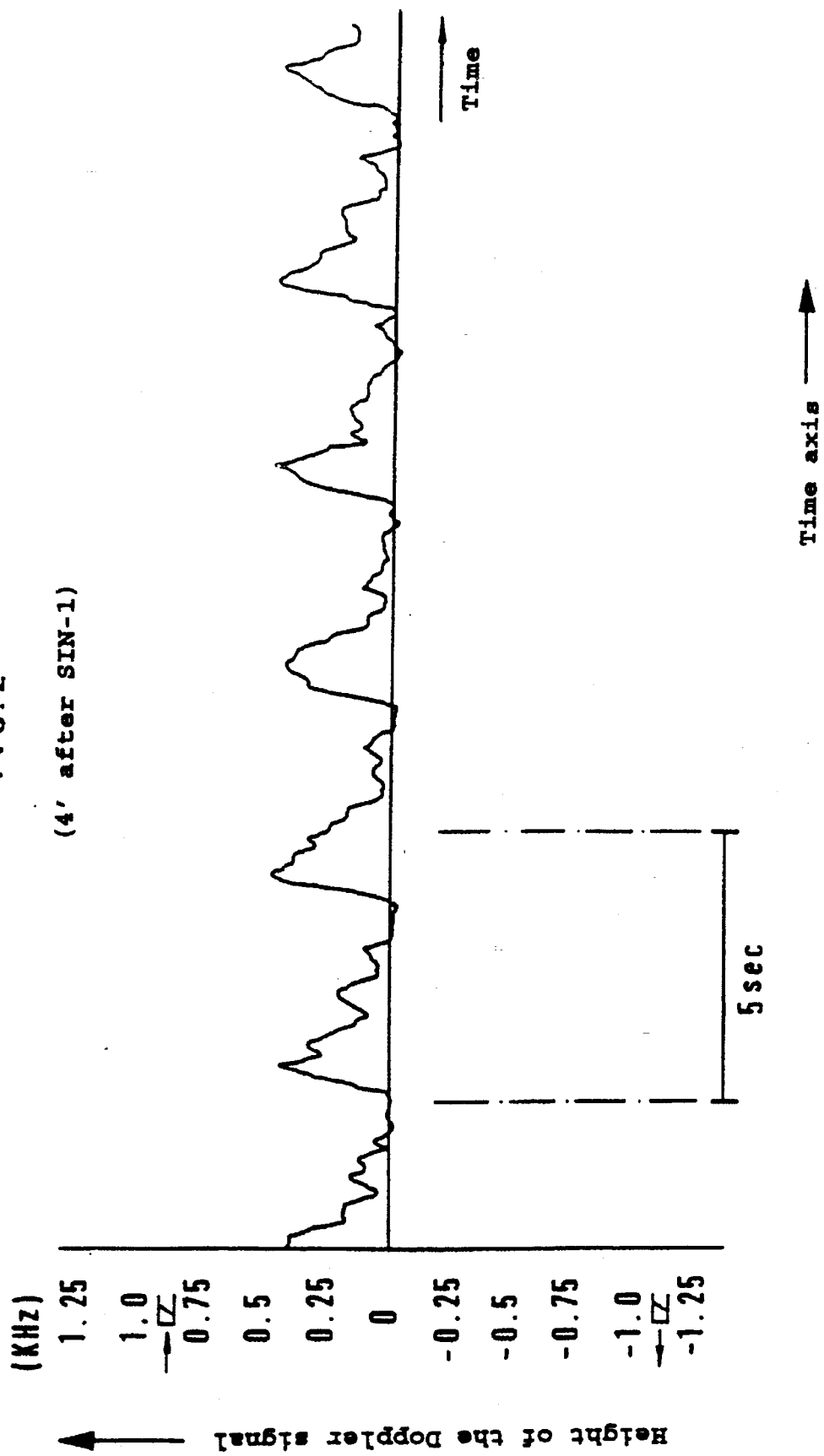
FIG. 2 shows a state 4 minutes after intracavernous injection of 0.2 mg of linsidomine hydrochloride in the form of a powerful signal with a markedly increased blood flow and onset of erection.
Figure 3:
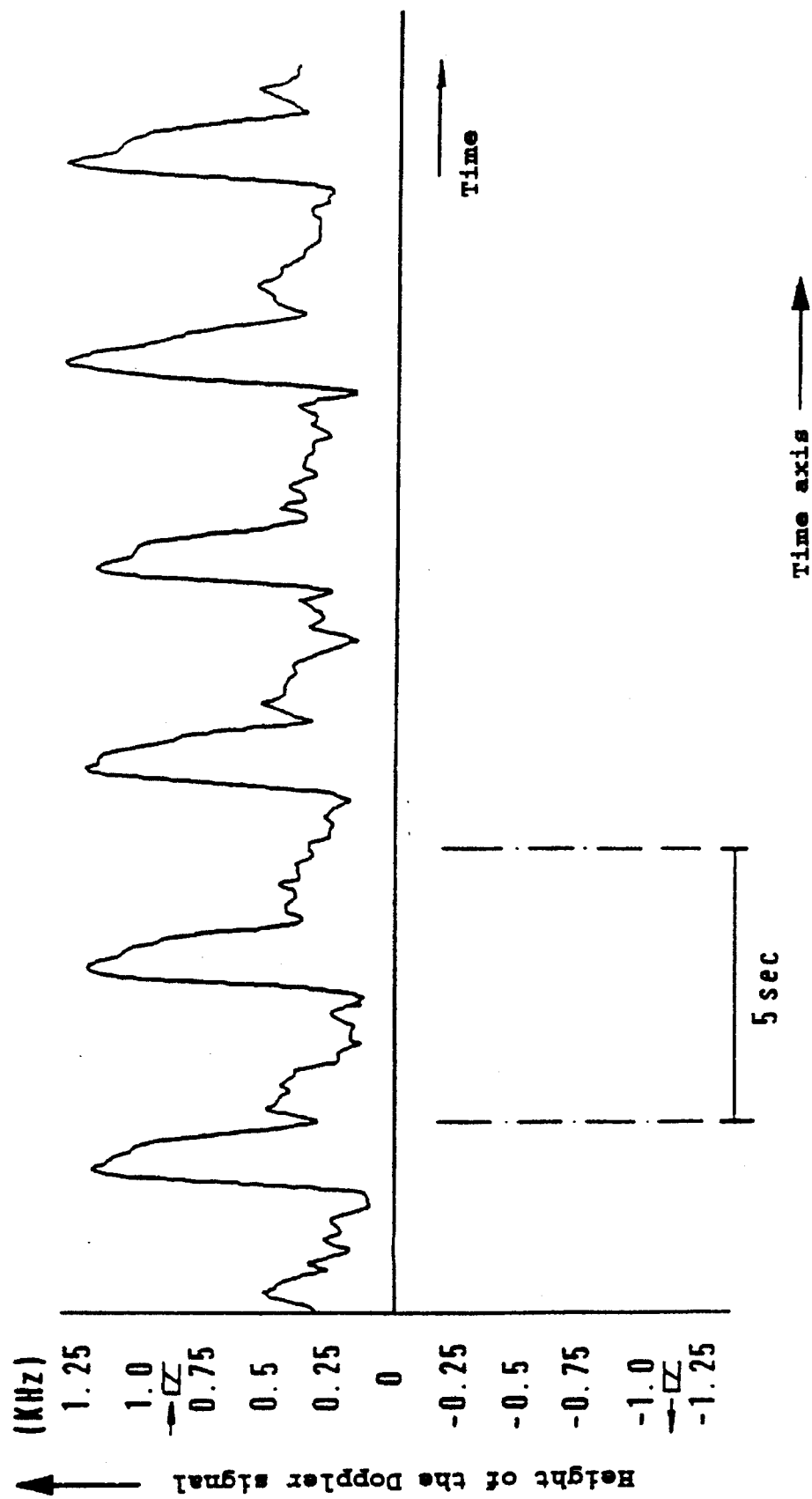
FIG. 3 shows a very powerful Doppler signal with increasing erection 7 minutes after injection.
Figure 4:
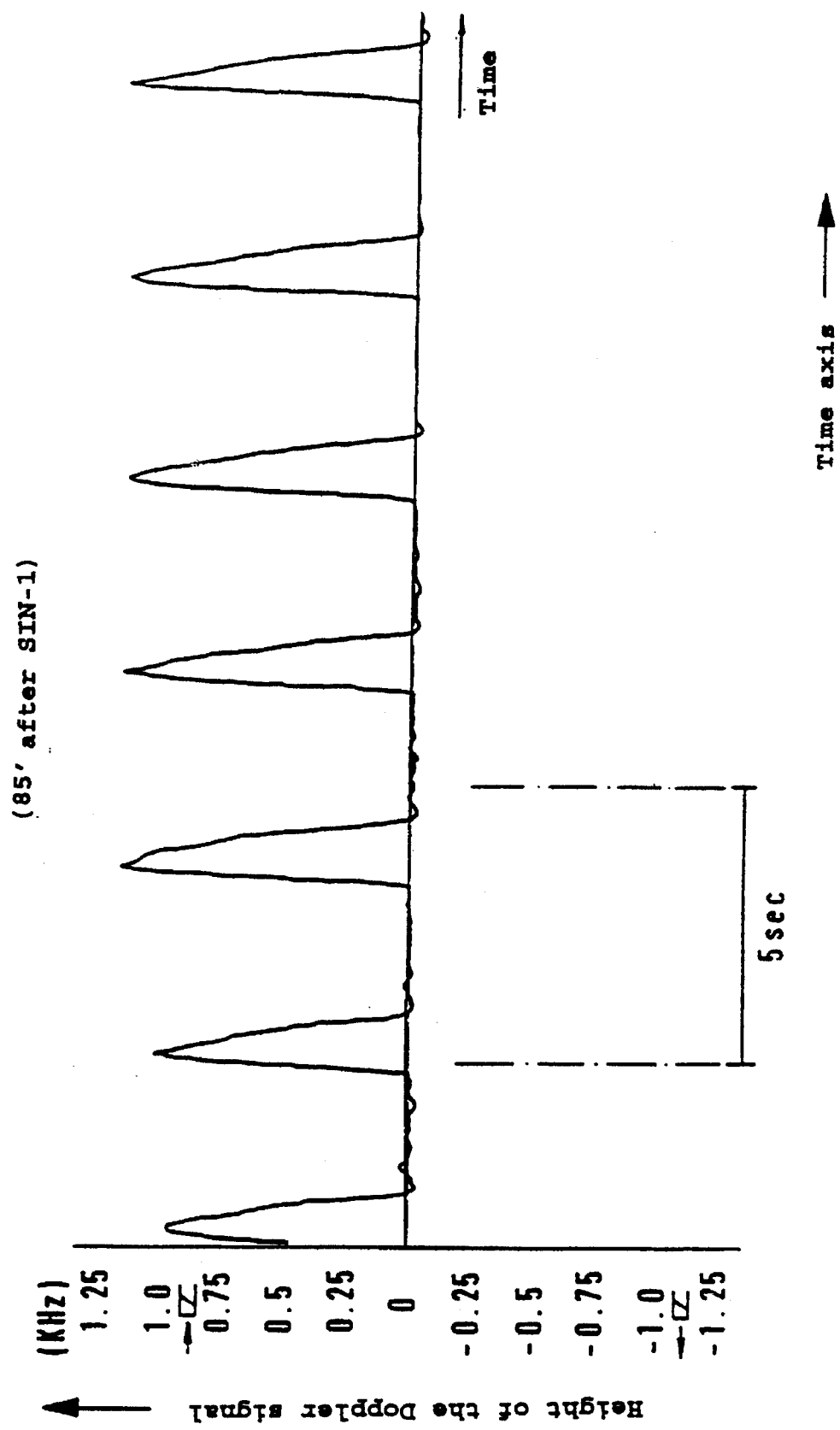
FIG. 4 shows a still marked increase in blood flow with diminishing complete erection 85 minutes after the injection.

The use of linsidomine in the treatment of erectile dysfunction represents, on the basis of these results, a considerable advance in cavernous body autoinjection therapy (CBAT), the standard form of treatment for erectile dysfunction (Stief, Urologe A, 25, 63, 1986). The release of nitric oxide from linsidomine and thus EDRF takes place non-enzymatically inside the cavernous tissue. This conversion limits the duration of the activity in the induction of an erection. The most hazardous side effect to date of cavernous body autoinjection therapy, prolonged erection with the risk of eventual impotence, is thus eliminated. Treatment of erectile dysfunction with linsidomine thus provides optimal therapeutic efficacy with, at the same time, a lower rate of side effects because linsidomine is also the active metabolite of molsidomine which has been employed and investigated in cardiovascular therapy for a long time now.

I claim:

1. Process for the treatment of human sexual impotence which comprises administering to a host in need thereof an effective dose of linsidomine or a pharmacologically compatible salt thereof.

2. Process according to claim 1 which comprises administering said linsidomine or salt thereof in combination with adenosine.

3. Process according to claim 1 characterized in that said effective dose comprises about 0.1 to 5 mg of linsidomine.

4. Process according to claim 1 which comprises administering said linsidomine or salt thereof in combination with one or more vitamins.

5. Process according to claim 1 which comprises administering said linsidomine or salt thereof in combination with one or more prostaglandins.

6. Process according to claim 1 which comprises administering said linsidomine or salt thereof in combination with one or more calcium antagonists.

7. Process according to claim 1 which comprises administering said linsidomine or salt thereof in combination with one or more $\alpha$-receptor blockers.

8. Process according to claim 1 which comprises administering said linsidomine or salt thereof in combination with one or more smooth muscle relaxants.

9. Disposable medicament pack for use in the treatment of human sexual impotence containing in a sterile package a disposable syringe with a parenteral formulation of a dose unit of one or more erection-promoting active substances selected from the group consisting of linsidomine and salts thereof, sterile swabs provided with disinfectants, and instructions for use.

10. Disposable medicament pack according to claim 9, characterized in that the active substance is linsidomine hydrochloride.

11. Disposable medicament pack according to claim 9, characterized in that the amount of active substance is 2 mg.

* * * * *